(12) United States Patent
Smart

(10) Patent No.: US 8,757,737 B2
(45) Date of Patent: Jun. 24, 2014

(54) MEDICAL CONTAINER

(75) Inventor: William Hugh Dawkins Smart, Buderim (AU)

(73) Assignee: Smartline Machinery Pty Ltd, Palmwoods, Queensland (AU)

(*) Notice: Subject to any disclaimer, the term of this patent is extended or adjusted under 35 U.S.C. 154(b) by 188 days.

(21) Appl. No.: 13/320,338

(22) PCT Filed: May 14, 2010

(86) PCT No.: PCT/AU2010/000571
§ 371 (c)(1),
(2), (4) Date: Feb. 1, 2012

(87) PCT Pub. No.: WO2010/130010
PCT Pub. Date: Nov. 18, 2010

(65) Prior Publication Data
US 2012/0139398 A1 Jun. 7, 2012

(30) Foreign Application Priority Data
May 14, 2009 (AU) .................................. 2009902165

(51) Int. Cl.
*A24F 25/00* (2006.01)
(52) U.S. Cl.
USPC ....................................................... 312/31.2
(58) Field of Classification Search
USPC ................. 312/31.2, 209, 237, 352; 600/102; 55/385.2, 473; 422/1, 33, 40
See application file for complete search history.

(56) References Cited

U.S. PATENT DOCUMENTS

| 4,832,717 | A | * | 5/1989 | Peters | 55/473 |
| 5,225,160 | A | * | 7/1993 | Sanford et al. | 422/28 |
| 6,797,681 | B2 | * | 9/2004 | Fricker et al. | 510/161 |
| 6,884,392 | B2 | * | 4/2005 | Malkin et al. | 422/26 |
| 7,959,871 | B2 | * | 6/2011 | Jonsson | 422/292 |
| 8,414,471 | B2 | * | 4/2013 | Mandava et al. | 600/102 |
| 2002/0001537 | A1 | * | 1/2002 | Hlebovy et al. | 422/28 |
| 2007/0154346 | A1 | * | 7/2007 | Lin et al. | 422/28 |

FOREIGN PATENT DOCUMENTS

| CN | 201019849 | | 2/2008 | | |
| FR | 2935603 | A1 * | 3/2010 | | A61L 2/26 |
| GB | 2364622 | | 5/2004 | | |
| JP | 2002282200 | A * | 10/2002 | | A61B 1/00 |
| JP | 2005052199 | | 3/2005 | | |
| JP | 2006333954 | | 12/2006 | | |

* cited by examiner

*Primary Examiner* — Hanh V Tran
(74) *Attorney, Agent, or Firm* — Dilworth & Barrese, LLP.

(57) ABSTRACT

A medical cabinet for storage of flexible scopes is in the form of a housing having an inlet to allow air to pass into housing and an outlet to allow air to pass out of the housing, with a pump to pump air into the housing via the inlet, a vacuum to suck air from the housing through the outlet, and an outlet connector connected to the outlet and also connectable to a port of at least one of the scopes. The outlet connector includes a vacuum pole, which extends substantially to the height of the housing. A method of storing a flexible scope by pumping air into the flexible scope located in a housing and sucking air through the flexible scope located in the housing is also provided.

20 Claims, 2 Drawing Sheets

MEDICAL CONTAINER

FIELD OF THE INVENTION

This invention relates to a medical container. In particular, the invention relates to a medical container for the storage of flexible scopes, such as endoscopes, colonoscopes and gastroscopes. However, it should be appreciated that the medical container can be used for other purposes.

BACKGROUND OF THE INVENTION

Flexible scopes, such as endoscopes, colonoscopes and gastroscopes, are commonly used throughout the world for both diagnostic and treatment purposes. As flexible scopes are expensive to manufacture and hence to purchase, flexible scopes are normally reused. This entails an extensive cleaning process after each use.

However, this is not the only time that flexible scopes are cleaned. In most countries throughout the world, flexible scopes must be cleaned after period of storage (typically 24 hours). For example, if a scope was used on a Friday and cleaned on a Friday, the scope must be re-cleaned before use on the Monday.

Cleaning of the flexible scopes decreases the life of the flexible scope. That is, the more times the scope is cleaned, the shorter the lifespan of the flexible scope. Another common way in which the lifetime of the scopes is reduced, is by storing the flexible scopes in a coil. This places stress on the internals of the scope and also allows liquids located internally in the scope to pool. This can create bacterial growth which can lead to patient infection which is major reason why scopes must be re-cleaned after a period of storage.

OBJECT OF THE INVENTION

It is an object of the invention to overcome and/or alleviate one or more of the above disadvantages or to provide the consumer with a useful or commercial choice.

SUMMARY OF THE INVENTION

In one form, the invention resides in a medical cabinet for storage of flexible scopes, the medical cabinet comprising:
a housing having an inlet to allow air to pass into housing and an outlet to allow air to pass out of the housing;
a pump to pump air into the housing via the inlet;
a vacuum to suck air from the housing through the outlet; and
an outlet connector connected to the outlet and also connectable to a port of at least one of the scopes.

The housing preferably has a pivotally mounted door to allow a flexible scope to be placed within the housing.

Typically the pump and/or vacuum are located external to the housing. The pump and/or vacuum may be removable from the respective inlet and/or outlet. Normally, the pump and/or vacuum are located in a separate power unit. The unit may be used to supply power to the pump and/or vacuum.

The volume of air being pumped into the housing may be greater than the volume of air being sucked from the housing. The housing is normally positively pressurised.

The at least one outlet connector preferably includes a vacuum pole, which extends substantially to the height of the housing. Typically, attachment hoses extend from the pole for attachment to a port of a flexible scope.

A filter may be located between the pump and the inlet. The filter may be used to filter impurities from the air. Preferably the filter is a HEPA filter.

At least one hanger may be located within the container for hanging flexible scopes. The at least one hanger may be located on the pole. The at least one hanger may be rotatable with respect to the pole.

In another form, the invention resides in a housing forming part of a medical container for the storage of flexible scopes, the housing comprising:
an inlet to allow air to pass into housing;
an outlet to allow air to pass out of the housing; and
an outlet connector connected to the outlet and also connectable to a port of at least one of the scopes.

In yet another form the invention resides in a separate power unit forming part of a medical container for the storage of flexible scopes, the separate power unit comprising:
a pump to pump air into a housing of the medical container via an inlet; and
a vacuum to suck air from the housing of the medical container through an outlet.

In another form, the invention resides in method of storing a flexible scope, the method including the steps of:
pumping air on to the flexible scope located in a housing; and
sucking air through the flexible scope located in the housing.

The method may further include the steps of filtering the air that passes into the housing.

BRIEF DESCRIPTION OF THE DRAWINGS

Embodiments, by way of examples only, will be described with reference to the accompanying drawings in which.

DETAILED DESCRIPTION OF THE PREFERRED EMBODIMENT

Figure 1:
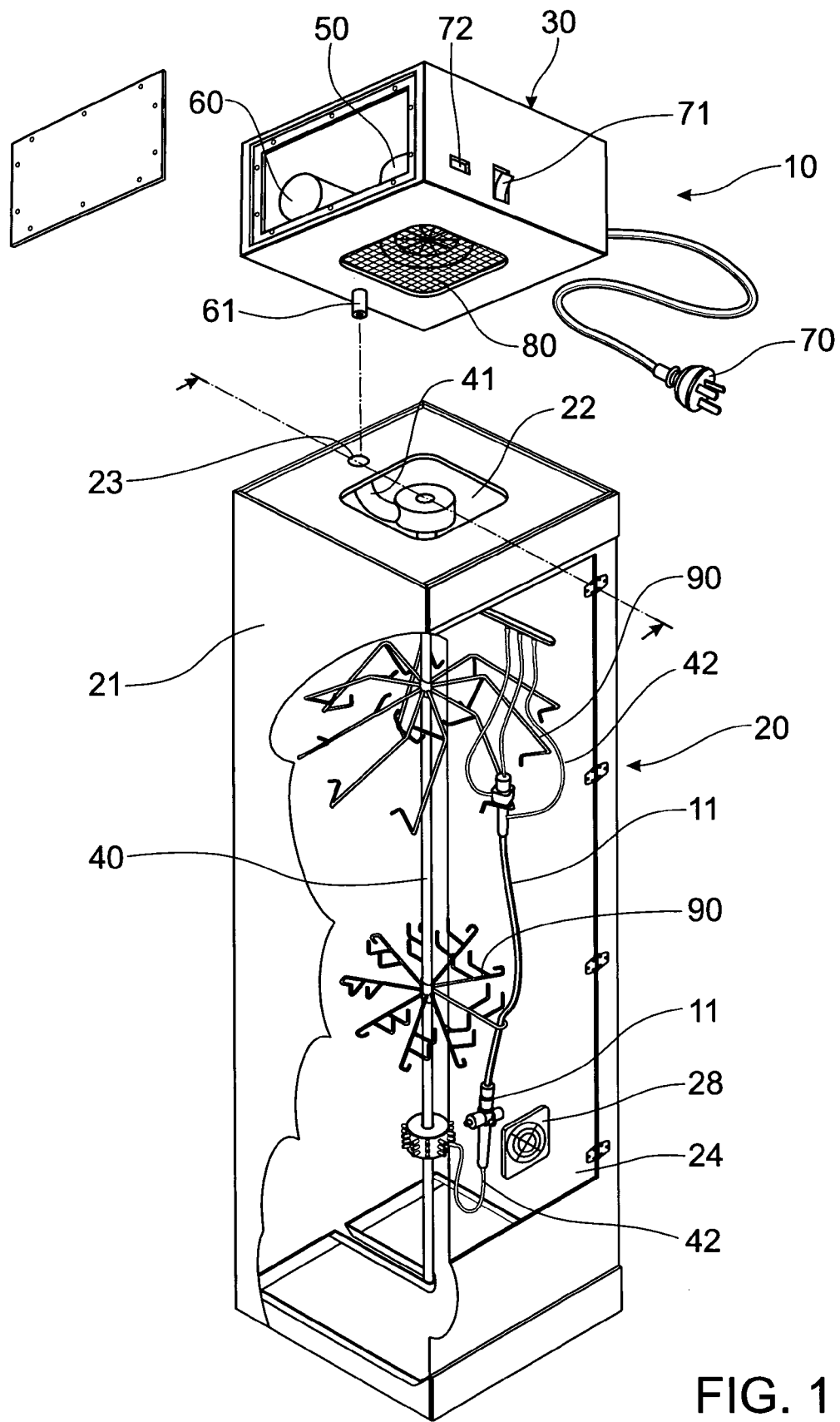
FIG. 1 is a perspective view of a medical container for the storage of flexible scopes according to an embodiment of the invention.
Figure 2:
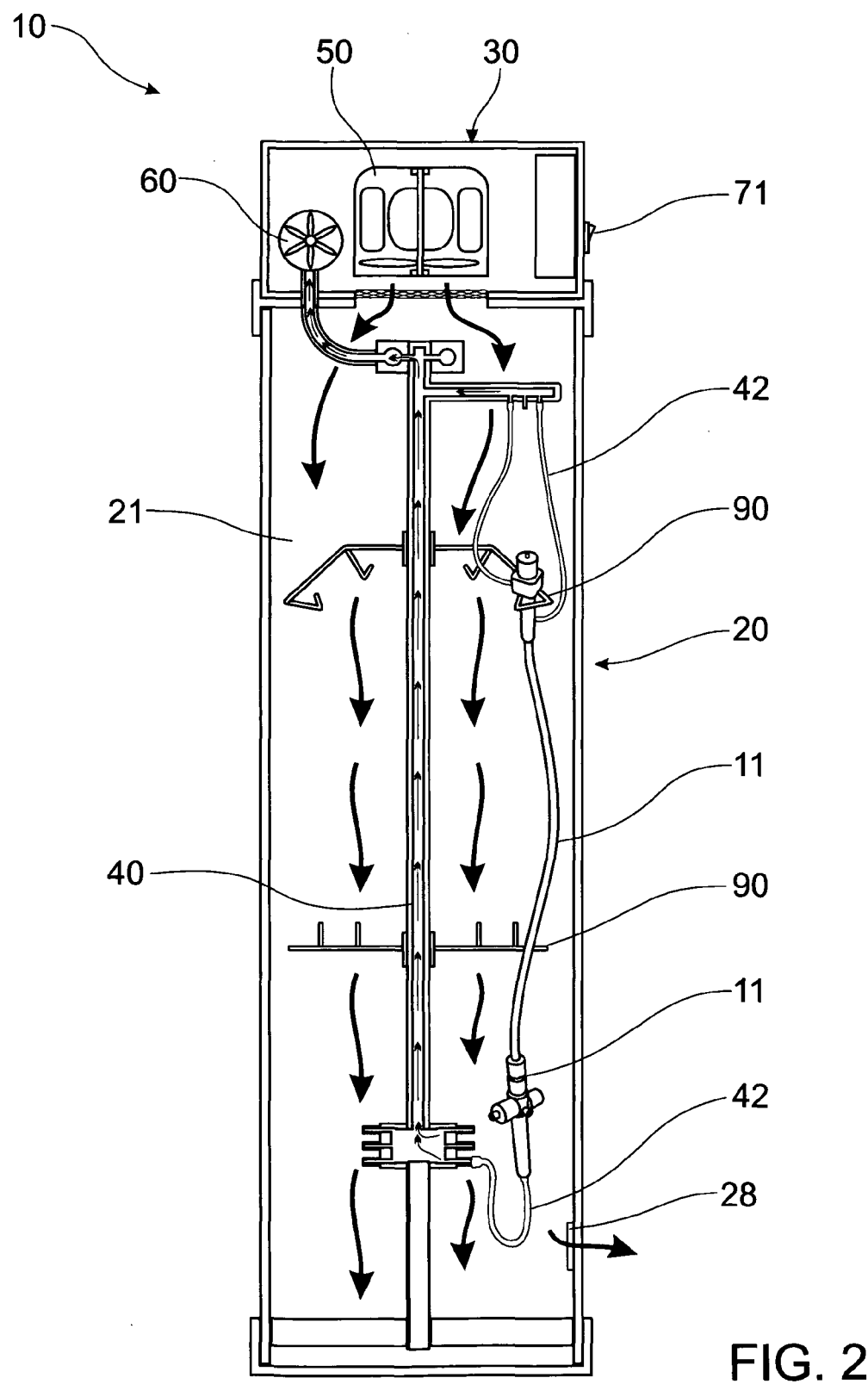
FIG. 2 is a sectional view of the medical container of FIG. 1 according to an embodiment of the invention.

FIG. 1 shows a perspective view of a medical container 10 used for storing flexible scopes 11, such as endoscopes, colonoscopes and gastroscopes. The medical container 10 is formed from a housing 20 and a separate power unit 30.

The housing 20 is formed from a rectangular hollow box 21 which has a pivotally mounted door 24. The housing 20 has an inlet 22 located at a top of the housing to allow air to flow into the housing 20. The housing 20 also has an outlet 23 that allows air to pass out of the housing 20. It should be appreciated that the housing 20 may be formed from a variety of materials known in the art.

A vacuum pole 40 is fluidly connected to the outlet 23 via a pole hose 41 and extends the height of the housing 20. Several attachment hoses 42 extend from and are fluidly connected to the vacuum pole 40. The attachment hoses 42 are designed to be connected to ports formed within the flexible scope 11. It should be appreciated that the design of the ports may vary depending on the type and manufacture of the flexible scope 11.

The separate power unit 30 is removably attached to the top of the housing 20. The separate power unit 30 contains a pump 50 and a vacuum 60. The pump 50 is fluidly connected to the inlet 22 of the housing 20. The vacuum pole 40 is fluidly connected to the outlet 23 via a connection pipe 61 forming part of the separate power unit 30. A power cord 70 is used to connect to the separate power unit 30 to an electric socket to supply power to the pump 50 and vacuum 60. A power switch 71 is used to control the power supplied to the pump 50 and vacuum 60. An indicator light 72 is located adjacent the power switch 71 to show when the power switch 71 is on and/or off.

A filter 80 is located within a base of the separate power unit 30 to filter air which passes into the housing 20. However, it should be appreciated that the filter 80 may be located over the inlet 22 on the housing 20 to produce a similar effect. The filter 80 is HEPA filter.

Two spaced apart, flexible scope hangers 90 are located on the vacuum pole 40 to hold flexible scopes 11. The hangers 90 can hold up to nine flexible scopes 11. However, it should be envisaged that the hangers 90 may be designed to hold more or less flexible scopes 11.

In use, the pump 50 and the vacuum 60 are in operation prior to a flexible scope 11 being placed into the housing 20. A flexible scope 11 is positioned in the housing 20 via a pivotal door 24 on the hangers 90 after it has been cleaned. Once the flexible scope 11 has been placed on to the hangers 90, ports of the flexible scope 11 are connected to the attachment hoses 42. The flexible scope 11 can then be stored for a period of time.

The medical container 10 operates by pumping air via the pump 50 from the atmosphere through the HEPA filter 80 and into the housing 20. This clean air is used to dry and maintain the external part of the flexible scope 11. The vacuum 60 is used to dry and maintain the internal ports of the flexible scope 11 by sucking clean air located within the housing 20 through the ports of the flexible scopes 11 via the attachment hose 42, vacuum pole 40 and outlet 23.

The pump 50 pumps air into the housing 20 at a higher rate that the air that is sucked by the vacuum 60 from the housing 20. This produces a housing 20 which is positively pressurized. The housing 20 is not air tight, but is sufficiently sealed to maintain a positive pressure. A filter vent 28 is located within housing 20 to allow for any excess pressure build up within the housing 20. Accordingly, when the pivotal door 24 is opened, no unfiltered air is passes into the housing 20.

The medical container 10 provides an environment for flexible scopes 11 to be stored for several days (typically up to 72 hours) without the need to re-clean the flexible scopes 11. Accordingly, medical staff can be utilized elsewhere rather than cleaning the scopes before a procedure (less labour cost), less cleaning products are required (good for the environment) and there is little time lost wastage as the procedure can commence immediately.

It will also be appreciated that various other changes and modifications may be made to the embodiment described without departing from the spirit and scope of the invention.

The invention claimed is:

1. A medical cabinet for storage of flexible scopes, the medical cabinet comprising:
    a housing having an inlet to allow air to pass into the housing and an outlet to allow air to pass out of the housing;
    a pump to pump air into the housing via the inlet;
    a vacuum to suck air from the housing through the outlet; and
    an outlet connector connected to the outlet and also connectable to a port of at least one of the scopes,
    wherein the outlet connector includes a vacuum pole, which extends substantially the height of the housing.

2. The medical cabinet of claim 1 comprising a pivotally mounted door to allow a flexible scope to be placed within the housing.

3. The medical cabinet of claim 1 wherein the pump and/or vacuum is located external to the housing.

4. The medical cabinet of claim 1 wherein the pump is removable from the inlet.

5. The medical cabinet of claim 1 wherein the vacuum is removable from the outlet.

6. The medical cabinet of claim 1 wherein the pump and/or vacuum is located in a separate power unit.

7. The medical cabinet of claim 6 wherein the separate power unit is used to supply power to the pump and/or vacuum.

8. The medical cabinet of claim 1 wherein the volume of air being pumped into the housing is greater than the volume of air being sucked from the housing.

9. The medical cabinet of claim 1 wherein the housing is positively pressurized.

10. The medical cabinet of claim 1 wherein the vacuum pole has attachment hoses extending from the pole for attachment to a port of a flexible scope.

11. The medical cabinet of claim 1 wherein a filter is located between the pump and the inlet.

12. The medical cabinet of claim 11 wherein the filter is a HEPA filter.

13. The medical cabinet of claim 1 wherein at least one hanger is located within the housing for hanging of flexible scopes.

14. The medical cabinet of claim 13 wherein the at least one hanger is rotatably mounted on the vacuum pole.

15. The medical cabinet of claim 1, wherein the vacuum pole is mounted to direct air out from the housing after passing through at least one of the scopes.

16. A housing for use as part of a medical container for the storage of flexible scopes, the housing comprising:
    an inlet to allow air to pass into the housing;
    an outlet to allow air to pass out of the housing; and
    an outlet connector connected to the outlet and also connectable to a port of at least one of the scopes,
    wherein the outlet connector includes a vacuum pole, which extends substantially the height of the housing.

17. The housing as claimed in claim 16 wherein the vacuum pole has attachment hoses extending from the pole for attachment to a port of a flexible scope.

18. A method of storing a flexible scope, the method including the steps of:
    connecting both ends of the flexible scope to an outlet connector in a housing;
    pumping air on to the flexible scope located in the housing; and
    sucking air through the flexible scope located in the housing.

19. The method of claim 18 further including the step of filtering the air that passes into the housing.

20. The method of claim 18, wherein the housing comprises:
    an inlet to allow air to pass into the housing;
    an outlet to allow air to pass out of the housing; and
    an outlet connector connected to the outlet and also connectable to a port of at least one of the scopes.

* * * * *